(12) United States Patent
Carson

(10) Patent No.: US 6,377,856 B1
(45) Date of Patent: Apr. 23, 2002

(54) DEVICE AND METHOD FOR IMPLANTING MEDICAL LEADS

(75) Inventor: Dean F. Carson, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/332,535

(22) Filed: Jun. 14, 1999

(51) Int. Cl.⁷ .................................................. A61N 1/05

(52) U.S. Cl. ..................................................... 607/122

(58) Field of Search .................................. 607/115, 120, 607/122, 123, 121, 119

(56) References Cited

U.S. PATENT DOCUMENTS

| | | | | |
|---|---|---|---|---|
| 4,732,163 A | | 3/1988 | Bonello et al. | 128/772 |
| 5,531,783 A | | 7/1996 | Giele et al. | 607/126 |
| 5,697,965 A | * | 12/1997 | Griffin | 607/123 |
| 5,755,766 A | | 5/1998 | Chastain et al. | 607/122 |
| 5,843,028 A | | 12/1998 | Weaver et al. | 605/54 |
| 5,860,974 A | * | 1/1999 | Abele | 607/122 |

* cited by examiner

*Primary Examiner*—Scott M. Getzow
(74) *Attorney, Agent, or Firm*—Steven M. Mitchell

(57) ABSTRACT

An intravenous cardiac lead having a lumen for delivering a contrast agent as an aid in placement within the coronary sinus or a coronary vein. Also disclosed is a method for advancing such a lead through the right atrium and into the coronary sinus.

26 Claims, 5 Drawing Sheets

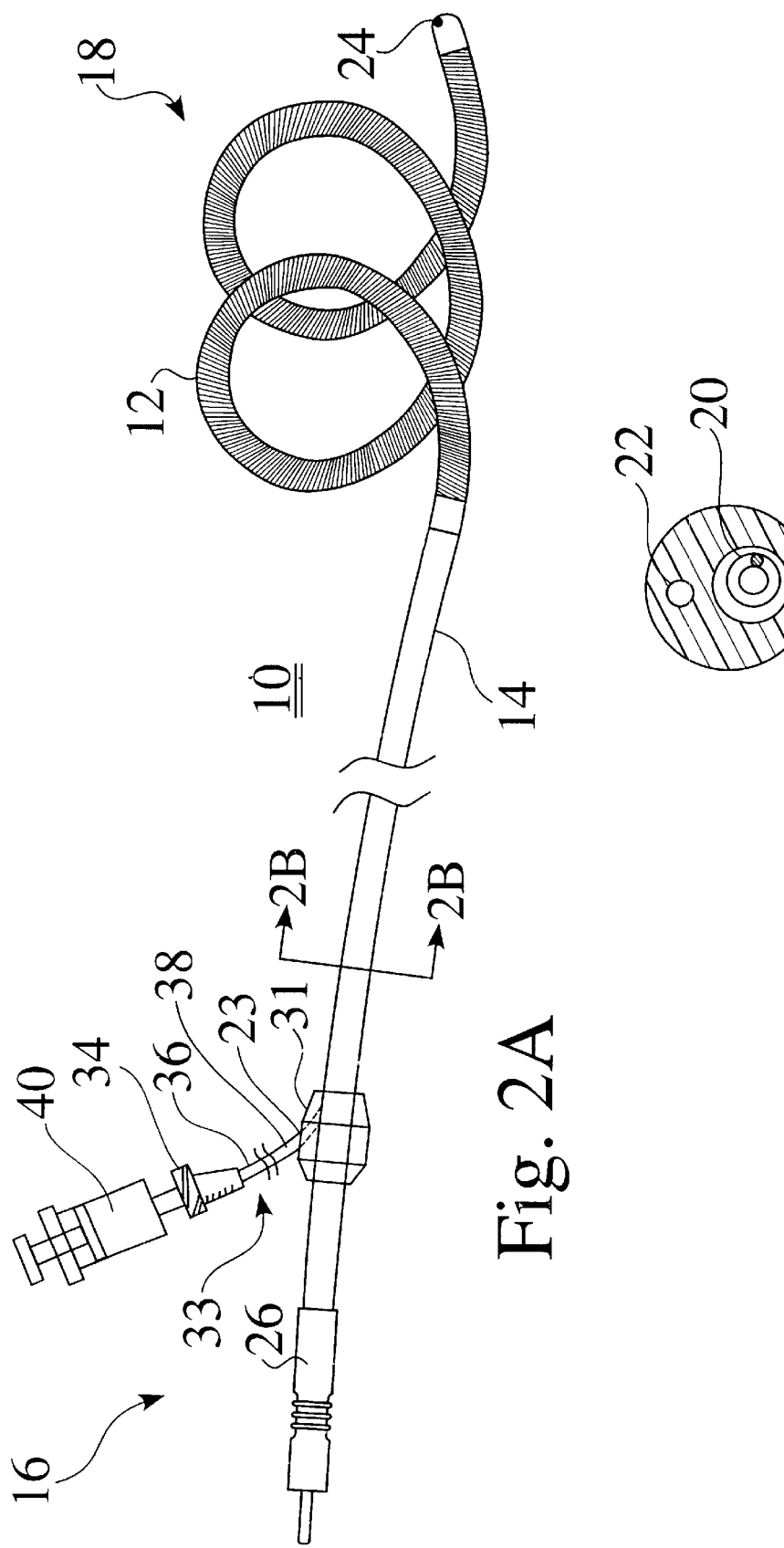

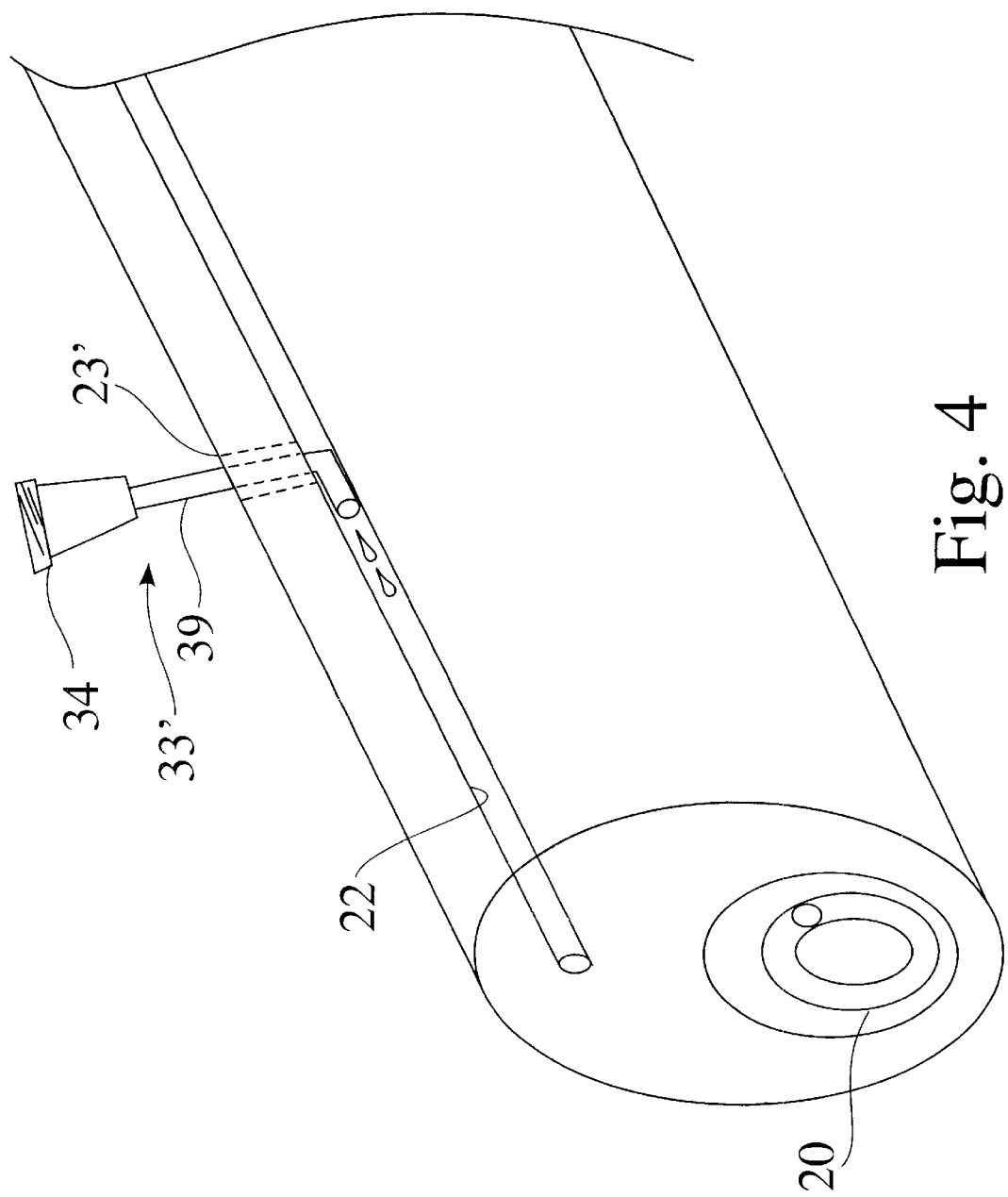

DEVICE AND METHOD FOR IMPLANTING MEDICAL LEADS

FIELD OF THE INVENTION

This invention relates to cardiac leads used in combination with a cardiac rhythm management device, e.g., heart pacemaker or defibrillator, to monitor and control the rhythm of the heart. This invention is more particularly directed toward transvenous lead configurations adapted to be implanted in the coronary sinus (CS) or a coronary vein and to methods for implanting such leads.

BACKGROUND OF THE INVENTION

Transvenous lead placement into the CS or deeper into the great cardiac vein or other coronary vein has recently become an important technique for cardiac pacing and defibrillation electrode implantation. For example, pacing the left ventricle (LV) from within a coronary vein appears to improve hemodynamics in certain heart failure patients. As another example, biatrial pacing, with the left atrium paced from the CS, is being studied to reduce the incidence of paroxysms of atrial fibrillation. As yet another example, defibrillation electrodes within the CS have been shown to reduce atrial and ventricular defibrillation thresholds.

U.S. Pat. No. 4,932,407 to Williams; U.S. Pat. No. 5,099,838 to Bardy; and U.S. Pat. Nos. 5,348,021; 5,433,729; and 5,350,404 to Adams et al., incorporated herein by reference, describe inserting a lead through the right atrium (RA) and CS into one of the coronary veins. None of these patents, however, discuss the difficulties encountered in doing so.

Fast and accurate placement of temporary or permanent leads into specific cardiovascular locations is difficult at best. For example, when the target location is the CS for left-sided pacing or defibrillation, the lead must follow a restrictive, tortuous path, and guidewire systems for leads are not yet capable of providing perfect control for simple placement. Current techniques practiced by implanting physicians usually involve guiding the lead to the desired location using tactile senses with fluoroscopic assistance.

These methods do not provide adequate feedback for consistently successful results. Furthermore, a semicircular valve, called the valve of Thebesius, protects the opening of the CS (the CS os), making it a difficult target. There is typically a learning curve associated with these procedures and thus there is a need for improved devices and methods for implanting leads. Furthermore, the profile of the distal end of a lead implanted in a coronary vein should be made as small as possible to limit occlusion of flow through the blood vessel when the lead is in place and to limit damage to the vessels. This requirement precludes the use of elaborate placement devices that add bulk to the lead.

U.S. Pat. No. 5,755,766 to Chastain et al. uses an existing lumen that houses a conductor for introducing a contrast agent as an aid in implanting the lead. One drawback to this arrangement is that if the existing conductor lumen is open from the connector to the patient's body, contrast agent (if not flushed), saline (from flushing), or blood (over the long term) may be allowed to enter into the header. This may lead to electrical shorting between connector blocks should sealing rings lose their seal or the encapsulation header material delaminate from the connector blocks and allow a fluid path between connections. In one embodiment of Chastain et al., a plug is deployed to close the distal opening and seal the lumen; this may prove difficult when working from the proximal end of the lead through a small lumen.

Furthermore, the structure of Chastain et al. limits delivery of the contrast agent to be from the distal tip of the lead. The present invention is not so limiting and permits the agent to be advantageously delivered radially from the side wall of the distal end of the lead.

It is therefore the object of this invention to provide both a device and a procedure that facilitate quicker, simpler, and more accurate lead placement into the desired final location, such as the CS or other cardiovascular structures.

SUMMARY OF THE INVENTION

The present invention provides an improved lead for implantation of an electrode into a coronary vein on the left side of the heart. The lead includes an elongated, flexible body member made of an electrically insulative material. The body member includes a proximal end and a distal end. A lumen extends through the body member from the proximal end toward the distal end. The lumen may extend all the way to the distal end so that the distal end includes an opening. The lead also includes a conductive member positioned alongside the lumen and extending through the body member from the proximal end toward the distal end. Electrically coupled to the conductive member near its distal end is an electrode. Additional lumens, electrodes and conductive members may be included within and on the lead body.

The cardiac lead of this invention has a lumen through which a radiopaque fluid may be injected. This lumen may be significantly smaller in diameter than other lumens used to house electrical conductors or accept stylets or guidewires, which are typically at least 0.014 inches in diameter. A radiopaque fluid is injected through the proximal end of the lumen and dispensed from a distal location, preferably as close to the distal tip as possible. A 0.003-inch diameter lumen would allow the passage of an appropriate commercially available radiopaque fluid. Thus, the overall diameter of the lead would not be significantly increased over a lead without such a lumen.

To implant a lead made in conformance with the present invention, the implanter passes the lead through a guide catheter, or introducer, until it is in or near the CS. This is done using a standard technique of stiffening the lead with a stylet, guiding the stiffened lead by hand through the RA and into or near the CS, aided by fluoroscopy. When the implanter wants to visually confirm that the lead is in the CS, he delivers a bolus of contrast agent through the small lumen and out the distal end of the lead. If the lead is in the CS, the bolus will be observed under fluoroscopy to travel back along the length of the lead, since the blood flow in the CS is returning to the RA and the lead will appear to be heading "upstream". If the lead is not in the CS but is still in the RA, the bolus will be seen squirting out from the tip in a forward manner before becoming diluted in the RA. Following proper placement, any stiffening stylets or guide catheters are retracted and the lumen may be flushed of all contrast agent with sterile saline.

The distal exit port may comprise a slit in the lead sidewall. This design prevents tissue ingrowth and maintains the patency of the lumen for possible future use.

The proximal end of the lead may incorporate a Luer lock that is detachable so it does not need to be implanted. The Luer lock may be connected to a short length of tubing having a lumen that forms a continuous channel with the lead body lumen for contrast delivery.

BRIEF DESCRIPTION OF THE DRAWINGS

FIG. 2A is a plan view of the intravenous cardiac lead shown in FIG. 1;

FIG. 2B is a cross-sectional view of the lead body shown in FIG. 2A;

FIG. 4 is an alternative embodiment of a proximal lumen opening of the lead of FIG. 1;

DETAILED DESCRIPTION OF THE INVENTION

Figure 1:
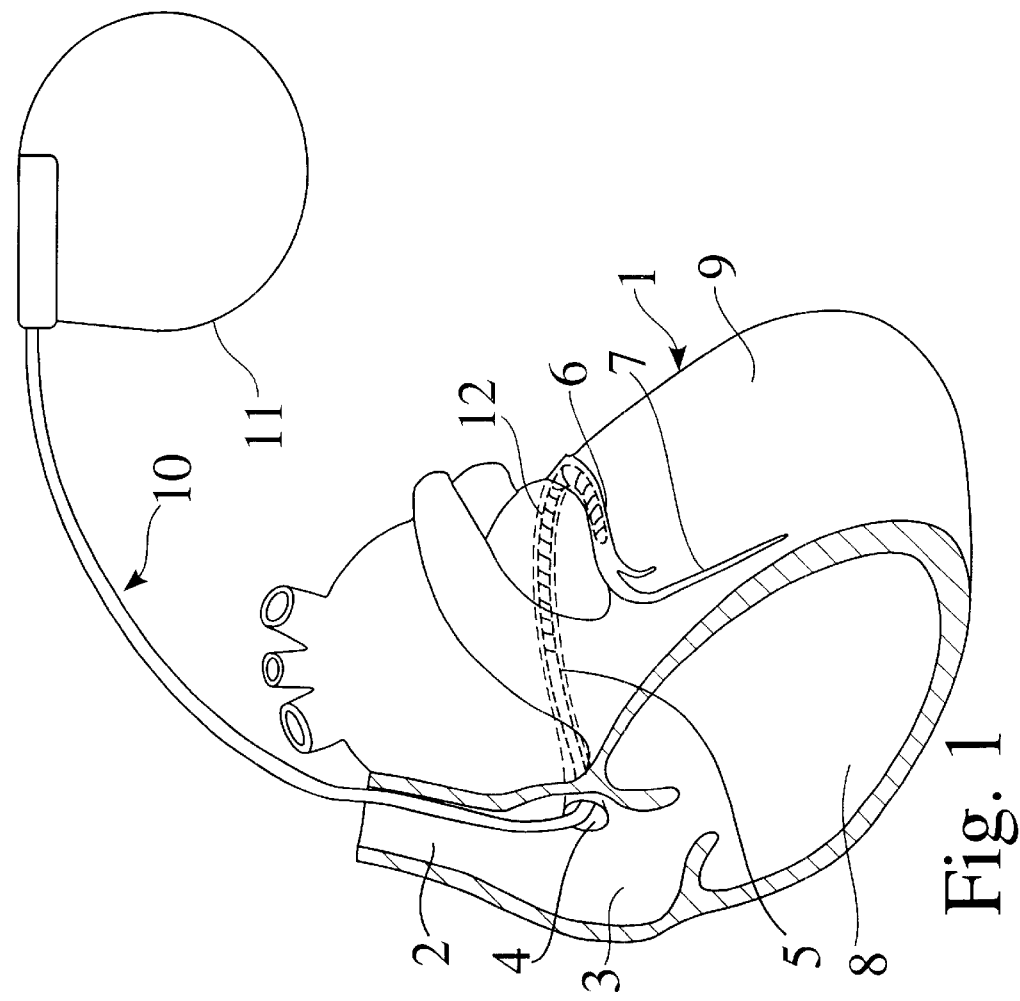
FIG. 1 is a plan view of an intravenous cardiac lead as implanted within the heart and with an electrode in the coronary sinus.

FIG. 1 shows a human heart 1 with the intravenous coronary lead 10 of the present invention passing through the superior vena cava (SVC) 2, the RA 3, the CS os 4 and the CS 5 into the great cardiac vein (GCV) 6 so that a surface electrode 12 on lead 10 is implanted within the GCV 6. In fact, electrode 12 may be positioned into a deeper coronary vein 7. When positioned as shown, electrode 12 can be used to sense the electrical activity of the heart or to apply a stimulating pulse to the LV 9 without the need of being in the left ventricular chamber.

FIGS. 2A and 2B show in greater detail the structure of intravenous coronary lead 10 shown in FIG. 1. As shown, lead 10 includes an elongated body member 14 having a proximal end 16 and a distal end 18. Body member 14 is preferably made of a flexible, electrically insulative material.

Body member 14 encapsulates a flexible electrically conductive member 20 extending from proximal 16 end toward distal end 18 of body member 14. Conductive member 20 is shown as a flexible wire coil. Alternatively, conductive member 20 may be in the form of a conductive wire, a plurality of fine wires formed as a cable, or a flexible tube without deviating from the invention. Furthermore, conductive member 20 may reside within a lumen of body member 14 or may be embedded within body member 14 without significant air space between conductive member 20 and the encapsulating material of body member 14.

FIGS. 2A and 2B also show the lead as including a lumen 22 extending from proximal end 16 to distal end 18 of body member 14 and lying alongside and approximately parallel to conductive member 20. In this embodiment, there is a first opening 23 through proximal end 16 to lumen 22 and a second opening 24 through distal end 18 to lumen 22. Alternatively, second opening 24 may be located elsewhere on the lead, as will be discussed later. Lumen 22 is preferably between 0.003 and 0.010 inches in diameter, which is significantly smaller in diameter than typical lumens used to house electrical conductors or guidewires. This lumen is used to inject a contrast agent 40 such as a radiopaque fluid to facilitate fluoroscopic viewing. A radiopaque fluid is injected through the proximal end of the lumen and dispensed from a distal location, preferably as close to the distal tip as possible. Appropriate radiopaque fluids are commercially available.

The electrode 12 is shown as a flexible, large surface area electrode electrically coupled to conductive member 20, and suitable for atrial or ventricular defibrillation. The position of electrode 12 along body member 14 can be changed. Alternatively or additionally, lead 10 may include one or more pacing or sensing electrodes for implantation within the CS. Additionally, lead 10 may include one or more pacing, sensing, or defibrillation electrodes for placement within the SVC or RA.

Lead 10 includes a connector 26 of a type known in the art at its proximal end for mating with the pacer and/or defibrillator pulse generator whereby depolarization signals originating in the heart can be sensed and pacing or defibrillating pulses applied in accordance with the device's control algorithms. Connector 26 is electrically coupled to conductive member 20.

Figure 3A:
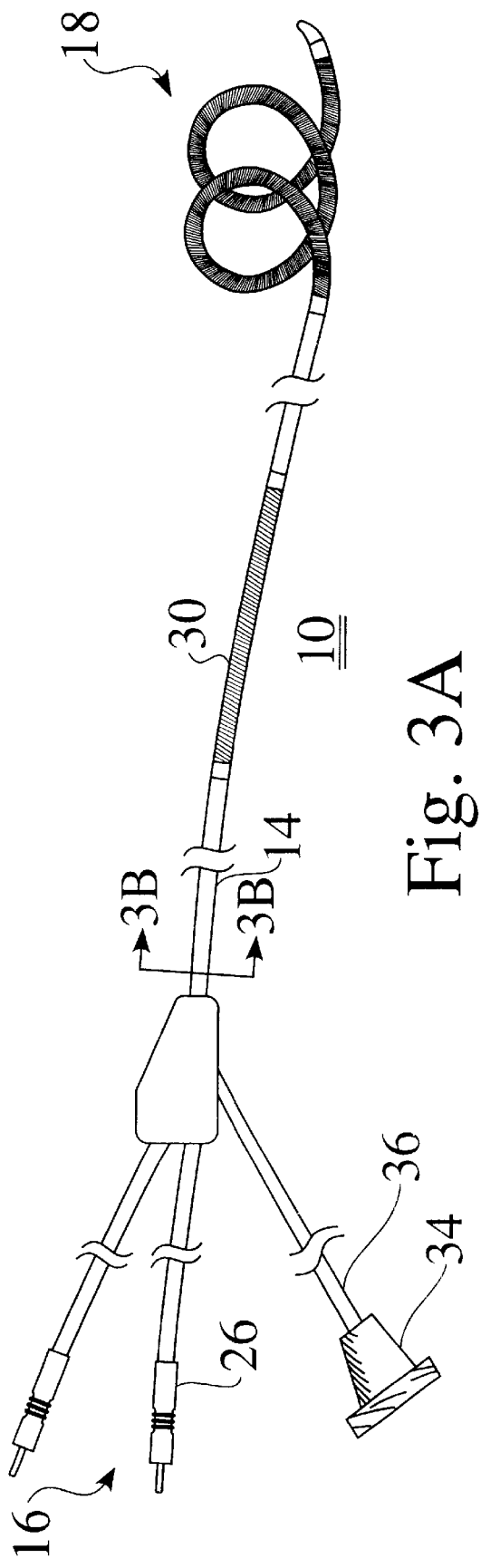
FIG. 3A is a plan view of an intravenous coronary lead of the present invention.
Figure 3B:
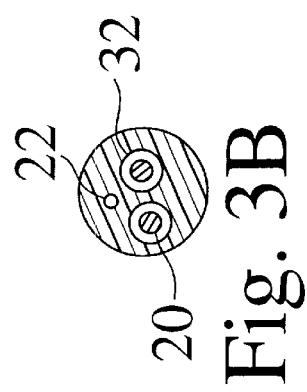
FIG. 3B is a cross-sectional view of the lead body shown in FIG. 3A.

FIGS. 3A and 3B also show how lead 10 can be modified to provide an additional, more proximal defibrillation electrode 30 for placement within the SVC or RA. The proximal defibrillation electrode 30 is electrically coupled to an additional conductive member 32. Even more electrodes and conductors can be added for sensing, pacing or defibrillating as desired. Electrodes such as electrodes 12 and 30 may be multipurpose and may be used for sensing electrical activity of the heart, and/or unipolar or bipolar pacing, in addition to or instead of atrial or ventricular defibrillation. The proximal portion of body member 14 may have a larger diameter than the distal portion that is intended for placement through the CS os. For example, the proximal portion of body member 14 may have an outside diameter in the range of 0.020 inches to 0.100 inches and the more distal portion may have a smaller outside diameter such as 0.010 inches to 0.050 inches.

To implant a lead made in conformance with the present invention, a guide catheter or introducer may be inserted through a vein such as an axillary vein, a subclavian vein, or an internal or external jugular vein. Then the lead is passed through the guide catheter until it is in or near the CS using a standard technique of stiffening the lead with a stylet, guiding the stiffened lead by hand through the RA and into the CS, aided by fluoroscopy. The lead may also be connected to a monitor to monitor intracardiac electrograms as an aid in positioning, as is known in the art. When the implanter wants to visually confirm that the lead is in the CS, he delivers a bolus of contrast agent through the small lumen and out the distal end of the lead. If the lead is in the CS, the bolus will be observed under fluoroscopy to travel back along the length of the lead, since the blood flow in the CS is returning to the RA and the lead will appear to be heading "upstream". If the lead is not in the CS but is still in the RA, the bolus will be seen squirting out from the tip in a forward manner before becoming diluted in the RA. Following proper placement, any stiffening stylets or guide catheters are retracted and the lumen may be flushed of all contrast agent with sterile saline.

Standard contrast agents that are regularly used in cardiovascular fluoroscopic procedures may be used in this procedure, thereby not exposing the patient to any exotic new materials. Furthermore, this method should not increase the fluoroscopy time to which the patient is exposed. In fact, another advantage of this invention is that when the lumen is filled with contrast agent the lead body itself may be more easily viewed, potentially reducing time required for fluoroscopy.

Proximal end 16 may incorporate a fluid connector 31 that surrounds or forms the opening 23 to lumen 22. Fluid connector 31 is used to attach an injection port assembly 33 that is detachable so that it does not need to be implanted. Injection port assembly 33 may comprise a Luer fitting 34 connected to a short length of tubing 36 having a lumen 38 that forms a continuous channel with lumen 22 within the lead body.

FIG. 4 shows an alternative embodiment for the proximal lumen opening 23' and the attachable injection port assembly 33'. In this embodiment, the point of attachment is at the external surface of the lead body, and no additional fluid connector 31 is required. Lumen opening 23' comprises a self-sealing slit so as to maintain the isodiametric feature of the lead and eliminate any subcutaneous tissue ingrowth. Injection port assembly 33' comprises a Luer fitting 34 attached to a rigid, bent tube 29 having a blunt and/or soft tip whose outer diameter preferably is slightly larger than the diameter of lumen 22. This sizing forces contrast agent 40 and subsequent saline for flushing to be delivered toward the distal end of the lead. Following fluid delivery, injection port assembly 33' is removed and the slit seals itself. Either proximal lumen opening 23 or 23' and injection port assembly 33 or 33' may be located distal of the electrical connections to allow lead-to-pulse generator connections to be performed as usual.

Figure 5:
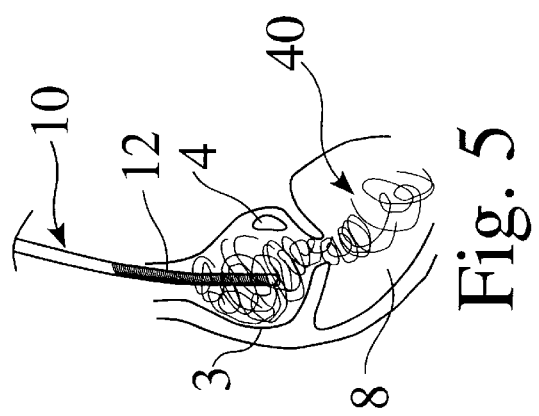
FIG. 5 is a view of the distal end portion of the intravenous cardiac lead shown in FIG. 1 in the right atrium while in the process of being implanted.
Figure 6:
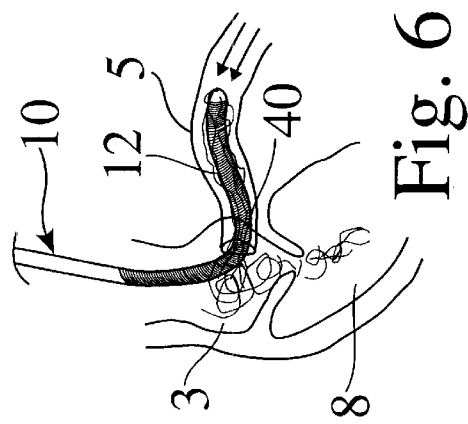
FIG. 6 is a view of the distal end portion of the intravenous cardiac lead shown in FIG. 1 in the coronary sinus while in the process of being implanted.

FIGS. 5 and 6 are provided to assist in explaining a method for implanting electrode 12 in the CS, GCV, or another coronary vein. FIG. 5 illustrates a fluoroscopic view of the lead of the present invention in the RA 3. A contrast agent 40 has been injected from lead 10 and has flowed into the right ventricle (RV) 8. The implanter can see from this fluoroscopic view that he must retract the lead slightly, then try to enter CS 5 through the CS os 4 such as by rotating lead 10.

FIG. 6 illustrates a fluoroscopic view of the lead in CS 5. Contrast agent 40 has been injected from lead 10 and is seen to be flowing back along its length with the low-pressure coronary sinus blood. (The direction of blood flow is shown by arrows in FIG. 6.) The implanter is thus reassured that he has entered the CS 5 and may proceed to insert the electrode as deeply as needed within CS 5, GCV, or into a coronary vein.

Figure 7:
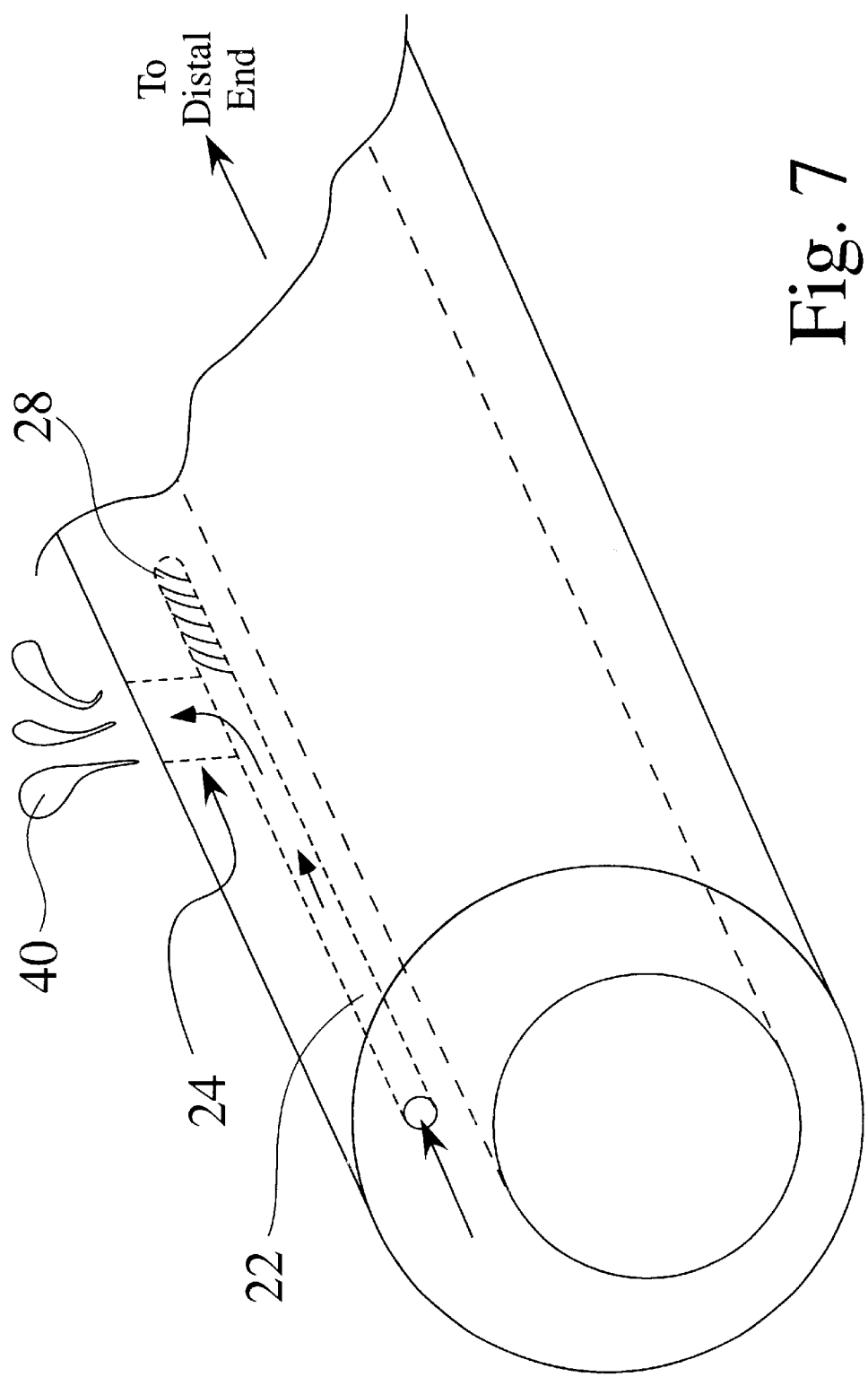
FIG. 7 is an alternative embodiment of the distal end of the lead of FIG. 1.

FIG. 7 illustrates an alternative embodiment of lead 10. Second opening 24 may comprise a slit in the lead sidewall instead of or in addition to the opening at the distal tip shown in FIGS. 2A, 2B, 3A, and 3B. One advantage of such a slit is that it may be normally closed, and only open when pressure is applied to deliver the contrast agent. Being normally closed prevents tissue ingrowth into the lumen and maintains the patency of the lumen for possible future use. As shown in FIG. 7, the distal end of lumen 22 may be plugged with a plug 28 so that contrast agent 40 may be ejected from only the slit.

The foregoing discussion is intended to illustrate various preferred arrangements for meeting the objectives of the present invention. Those skilled in the art can make modifications and variations without departing from the invention. For example, the lead of the present invention also may be implanted outside the CS, in which case, the lumen is used to inject a contrast agent to aid the implanter from inadvertently entering the CS. As another example, the lead may comprise an additional slit in a region of interest on the lead, such as near a pacing electrode whose location is critical. To illustrate, in biatrial pacing, it may be critical that a pacing electrode be located in the RA as close to the CS os as possible without crossing the valve of Thebesius and entering the CS through the CS os; a slit provided near that electrode could aid proper placement. Accordingly, the invention is limited only by the scope of the following claims.

What is claimed:

1. An implantable cardiac lead for connection to an implantable pacemaker or defibrillator comprising:
   (a) an elongated, flexible body member made of an electrically insulative material, said body member having a proximal end and a distal end;
   (b) a conductive member extending through said body member from said proximal end toward said distal end;
   (c) a contrast agent;
   (d) a lumen extending alongside said conductive member through said body member from the region of said proximal end toward said distal end, said lumen having a first opening proximate said proximal end and a second opening through said body member distal of said first opening so that said contrast agent can be injected through said lumen and out of said second opening; and
   (e) an electrode positioned on said flexible body member and electrically coupled to said conductive member.

2. The medical device of claim 1 wherein said conductor member comprises a coil.

3. The medical device of claim 1 wherein said second opening is proximate said distal end of said body member.

4. The medical device of claim 1 wherein said body member is of a size to permit the distal end to be advanced through the right atrium and coronary sinus os and into the coronary sinus.

5. The medical device of claim 4 wherein said body member is of a size to permit said distal end to be advanced into a coronary vein.

6. The medical device of claim 1 wherein said lumen has a diameter of between 0.003 inches and 0.010 inches.

7. The medical device of claim 1 and further comprising an injection port assembly for delivering said contrast agent into said lumen.

8. The medical device of claim 7 wherein said injection port assembly is detachable from said lead.

9. The medical device of claim 7 where in said injection port assembly comprises a Luer fitting.

10. The medical device of claim 1 wherein said first opening comprises a slit in the wall of said body member.

11. The medical device of claim 1 wherein said second opening comprises a slit in the wall of said body member.

12. The medical device of claim 8 wherein said injection port assembly comprises rigid tubing.

13. The medical device of claim 12 wherein said rigid tubing is bent.

14. The medical device claim 12 wherein said rigid tubing comprises a blunt tip.

15. The medical device claim 12 wherein said rigid tubing has an outer diameter larger than the diameter of said lumen.

16. The medical device of claim 7 and further comprising a fluid connector located proximate said first opening and adapted to connect to said injection port assembly.

17. A medical device system comprising:
   (a) an implantable pulse generator;
   (b) an implantable cardiac stimulation lead having
      an elongated, flexible body member made of an electrically insulative material, said body member having a proximal end and a distal end;

a conductive member extending through said body member from said proximal end toward said distal end;

a lumen extending alongside said conductive member through said body member from said proximal end toward said distal end, said lumen having a first opening through said proximal end and a second opening through said body member distal of said first opening so that a contrast agent can be injected through said lumen and out of said second opening; and an electrode electrically coupled to said conductive member; and (c) a contrast agent for delivery through said lead.

18. The medical device system of claim 17 wherein said second opening is proximate said distal end of said body member.

19. The medical device system of claim 17 wherein said lumen has a diameter of between 0.003 inches and 0.010 inches.

20. A method for implanting an intravenous lead comprising the steps of:

(a) inserting said lead through a vein;

(b) guiding said lead through the right atrium and proximate the CS;

(c) delivering a bolus of contrast agent through a lumen of said lead and observing a dispersion pattern of said contrast agent; and (d) using said dispersion pattern to determine a direction to move said lead.

21. The method of claim 20 and further comprising the step of stiffening said lead with a stylet.

22. The method of claim 20 wherein said step (c) includes determining that said dispersion pattern shows said bolus of contrast agent to travel back along the length of said lead, indicating that said lead is in the coronary sinus.

23. The method of claim 20 wherein said step (c) includes determining that said dispersion pattern shows said bolus of contrast agent to travel into the right atrium and then into the right ventricle, indicating that said lead has not crossed the coronary sinus os.

24. The method of claim 20 and further including the step of flushing said contrast agent from said lumen.

25. The method of claim 20 and further including the step of detaching an injection port assembly from said lead.

26. The method of claim 20 wherein said contrast agent is radiopaque and wherein said step of observing said dispersion is done using a fluoroscope.

* * * * *